United States Patent [19]
Spears

[11] Patent Number: 5,735,934
[45] Date of Patent: *Apr. 7, 1998

[54] METHOD FOR DELIVERING A GAS-SUPERSATURATED FLUID TO A GAS-DEPLETED SITE AND USE THEREOF

[75] Inventor: James Richard Spears, Bloomfield Hills, Mich.

[73] Assignee: Wayne State University, Detroit, Mich.

[*] Notice: The term of this patent shall not extend beyond the expiration date of Pat. No. 5,569,180.

[21] Appl. No.: 453,660

[22] Filed: May 30, 1995

Related U.S. Application Data

[60] Division of Ser. No. 273,652, Jul. 12, 1994, Pat. No. 5,569,180, which is a continuation-in-part of Ser. No. 152,589, Nov. 15, 1993, Pat. No. 5,407,426, which is a continuation-in-part of Ser. No. 818,045, Jan. 8, 1992, Pat. No. 5,261,875, which is a continuation of Ser. No. 655,078, Feb. 14, 1991, Pat. No. 5,086,620.

[51] Int. Cl.$^6$ .................................................. C21C 5/30
[52] U.S. Cl. ........................ 75/414; 75/559; 48/197 R; 62/66; 134/42; 162/1; 210/758; 435/818
[58] Field of Search .................. 75/559, 414; 48/197 R; 62/66; 134/42; 162/1; 210/758; 435/818

[56] References Cited

U.S. PATENT DOCUMENTS

| | | |
|---|---|---|
| 1,940,341 | 12/1933 | Bansen et al. ............... 75/559 |
| 2,975,606 | 3/1961 | Karwat. |
| 3,459,565 | 8/1969 | Jones et al.. |
| 3,963,503 | 6/1976 | Mackenzie. |
| 3,972,721 | 8/1976 | Hammel et al.. |
| 4,104,074 | 8/1978 | Resteker. |
| 4,285,977 | 8/1981 | Yezek et al.. |
| 4,303,432 | 12/1981 | Torobin. |
| 4,323,420 | 4/1982 | Masnari et al.. |
| 4,332,907 | 6/1962 | Viell. |
| 4,332,908 | 6/1982 | Viell. |
| 4,347,326 | 8/1982 | Iwami et al.. |
| 4,385,635 | 5/1983 | Ruiz. |
| 4,450,841 | 5/1984 | Osterholm. |
| 4,572,203 | 2/1986 | Feinstein. |
| 4,573,476 | 3/1986 | Ruiz. |
| 4,674,480 | 6/1987 | Lemelson. |
| 4,930,319 | 6/1990 | Bee et al.. |
| 4,963,130 | 10/1990 | Osterholm. |
| 4,969,878 | 11/1990 | Schmidt et al.. |
| 5,037,403 | 8/1991 | Garcia. |
| 5,044,164 | 9/1991 | Bee. |
| 5,072,739 | 12/1991 | John. |
| 5,086,620 | 2/1992 | Spears. |
| 5,116,317 | 5/1992 | Carson, Jr. et al.. |
| 5,261,875 | 11/1993 | Spears. |

*Primary Examiner*—Melvyn Andrews
*Attorney, Agent, or Firm*—Brooks & Kushman P.C.

[57] ABSTRACT

A method of injecting gas-supersaturated fluids as a bubble-free effluent from a delivery system into a relatively low pressure, gas-depleted environment without cavitation or bubble formation. The method includes the steps of eliminating cavitation nuclei from within the delivery system, compressing a fluid and a gas at a high partial pressure to form a gas-supersaturated fluid, and ejecting the gas-supersaturated fluid through the delivery system into the environment without associated cavitation formation in the effluent.

38 Claims, 1 Drawing Sheet

METHOD FOR DELIVERING A GAS-SUPERSATURATED FLUID TO A GAS-DEPLETED SITE AND USE THEREOF

CROSS-REFERENCE TO RELATED APPLICATIONS

This application is a division of Ser. No. 273,652 filed Jul. 12, 1994 now U.S. Pat. No. 5,569,180, which is a continuation-in-part of my application Ser. No. 152,589, filed Nov. 15, 1993, now U.S. Pat. No. 5,407,426, which is a continuation-in-part of application Ser. No. 07/818,045, filed Jan. 8, 1992 (now U.S. Pat. No. 5,261,875), which is a continuation of application Ser. No. 07/655,078, filed Feb. 14, 1991 (now U.S. Pat. No. 5,086,620). Each of these disclosures is incorporated by reference herein.

TECHNICAL FIELD

This invention relates to a method for delivering a gas-supersaturated fluid from a high pressure environment to a gas-depleted site at a lower pressure without the immediate onset of cavitation or bubbling.

BACKGROUND ART

The maximum concentration of gas achievable in a liquid ordinarily is governed by Henry's Law. At ambient pressure, the relatively low solubility of many gases, such as oxygen or nitrogen, within a liquid such as water produces a low concentration of the gas in the liquid. However, there are many applications wherein it would be advantageous to employ a gas concentration within the liquid which greatly exceeds its solubility at ambient pressure. Compression of a gas/liquid mixture at a high pressure can be used to achieve a high dissolved gas concentration, but disturbance of a gas-supersaturated liquid by attempts to eject it into a 1 bar environment from a high pressure reservoir ordinarily results in cavitation inception at or near the exit port. The rapid evolution of bubbles produced at the exit port vents much of the gas from the liquid, so that a high degree of gas-supersaturation no longer exists in the liquid at ambient pressure outside the high pressure vessel. In addition, the presence of bubbles in the effluent generates turbulence and impedes the flow of the effluent beyond the exit port.

In my co-pending application Ser. No. 152,589, filed Nov. 15, 1993, I described a method for stabilization of a stream of oxygen-supersaturated water which permitted ejection of the stream from a high pressure vessel into a 1 bar environment without cavitation inception in the effluent at or near the exit port(s). An effluent of water containing oxygen at a concentration on the order of 4 cc oxygen/g of injectate, representing a partial pressure of approximately 140 bar of the dissolved gas, can be ejected from a high pressure vessel into a 1 bar liquid environment with complete absence of cavitation inception in the ejected stream. In air at 1 bar, cavitation inception in a high velocity stream is delayed until breakup of the ejected stream into droplets.

The complete absence of cavitation inception in water supersaturated with oxygen at a high concentration permits its in vivo infusion into either venous or arterial blood for the purpose of increasing the oxygen concentration of blood without incurring the formation of bubbles which would otherwise occlude capillaries.

In addition to this application as previously described, a wide variety of other applications would benefit from ejection of a gas-supersaturated fluid from a high pressure reservoir into ambient pressure in a manner which is unassociated with cavitation inception at or near the exit port. For example, organic material and plant waste streams, e.g., paper mills and chemical plants, often require an increase in dissolved oxygen content before the discharge of such waste streams in a body of water. U.S. Pat. No. 4,965,022 also recognizes that a similar need may also occur at municipal waste treatment plants and that fish farms require increased dissolved oxygen levels to satisfy the needs of high density aquaculture. Other applications are disclosed in my U.S. Pat. No. 5,261,875.

U.S. Pat. No. 4,664,680 relates to enriching the oxygen content of water. That reference discloses a number of conventional types of apparatus that can be used for continuously contacting liquid and oxygen-containing gas streams to effect oxygen absorption. To avoid premature liberation of dissolved oxygen before it is incorporated within the bulk of matter to be enriched in oxygen content, pressurizable confined flow passageways are used.

Other oxygen saturation devices are disclosed in U.S. Pat. Nos. 4,874,509; and 4,973,558. These and other approaches leave unsolved the need to infuse gas enriched fluid solutions from a high pressure reservoir toward a reaction site at a lower pressure without cavitation or bubble formation in the effluent at or near the exit port.

SUMMARY OF THE INVENTION

A method is described for ejection of gas-supersaturated fluids or liquids from a high pressure reservoir to a relatively low pressure environment, including ambient pressure, which permits the use of the gas-supersaturated liquid at the lower pressure without immediate cavitation inception. Cavitation nuclei in the liquid are removed by compression in a high pressure reservoir. The use of suitable channels at the distal end of the system for delivery of the gas-supersaturated liquid, plus elimination of cavitation nuclei along the inner surface of the channels, allow ejection of the liquid into a relatively low pressure environment without cavitation inception at or near the exit port.

Thus, an important aspect of the invention described herein is the use of capillary channels at the distal end of the delivery system, along with initial hydrostatic compression of a liquid to remove cavitation nuclei along the inner surface of the channels. When such nuclei contain a relatively insoluble gas, such as oxygen or nitrogen, a hydrostatic pressure of 0.5 to 1.0 kbar is highly effective for this purpose. For nuclei of a soluble gas, such as carbon dioxide, a lower hydrostatic pressure can be used for their dissolution. Cavitation nuclei and bubbles in the bulk liquid are removed in the high pressure reservoir by either direct hydrostatic compression, for example, from movement of a liquid or piston driven by a hydraulic compressor, or by compression from a source of gas maintained at a pressure which would provide the desired concentration of gas in the liquid. Hydrostatic compression to 0.5 to 1.0 kbar rapidly removes cavitation nuclei and bubbles from the liquid, but much lower pressures from a gas source are also effective, although requiring longer periods of time. When a gas source is used to both pressurize the liquid and achieve a desired concentration of a relatively insoluble gas in the liquid, the range of gas pressure would typically be in the 10 bar to 150 bar range. When a highly soluble gas, such as carbon dioxide is used, a lower gas pressure, in the range of 2 to 5 bar would typically be employed.

As a result of the lack of cavitation inception at or near the exit port, a stream of gas-supersaturated liquid can be used to enrich a gas-deprived liquid with gas outside the high pressure reservoir simply by convection of the gas-supersaturated effluent with the gas-deprived liquid at ambient pressure. Enrichment of a gas-deprived liquid with gas by diffusion from the gas phase to the liquid is, by contrast, an extremely slow process. The lack of bubbles in the effluent additionally permits unimpeded ejection into the gas-deprived liquid. When the gas-supersaturated liquid is ejected in an air environment, the lack of cavitation inception at or near the exit port facilitates the use of the effluent in a manner similar to use of the same liquid which is not supersaturated with gas, i.e., the ejected stream remains intact, rather than becoming disintegrated into a diffuse spray near the exit port from rapid growth of gas nuclei.

Figure 1:
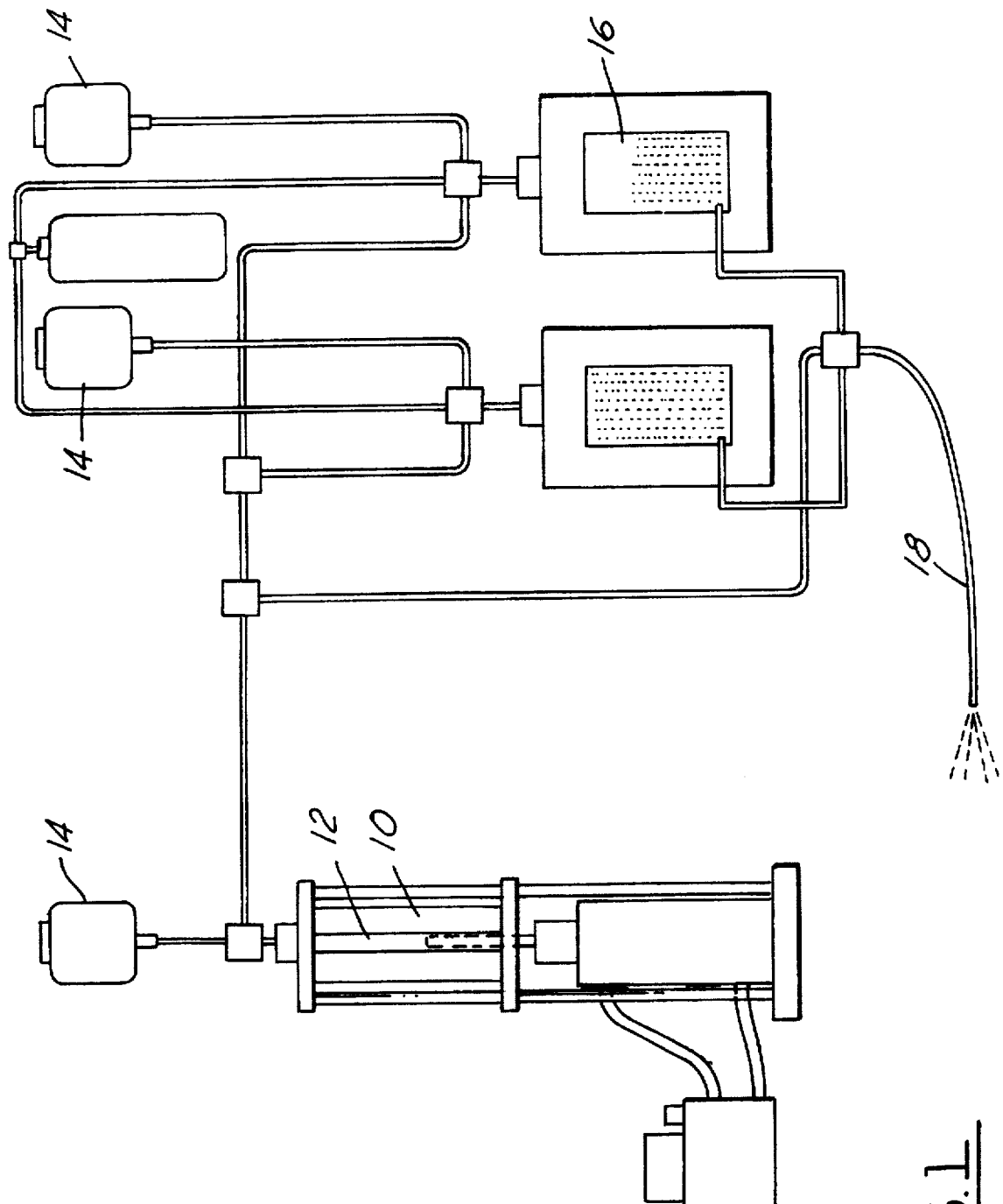
FIG. 1 depicts schematically a simplied configuration for delivering a gas-supersaturated fluid to a gas-depleted site without cavitation according to the present invention.

DETAILED DESCRIPTION OF THE PREFERRED EMBODIMENT AND BEST MODES FOR CARRYING OUT THE INVENTION

I now describe new aspects of my earlier work, along with representative examples of practical applications of the method.

In order to initiate flow of oxygen-supersaturated water through capillary channels, such as silica tubings, it had been necessary to use an internal diameter at the exit port on the order of 10 microns or less. However, it has been discovered that flow of gas-supersaturated water can resume or continue through a larger proximal portion of the capillary tubing, once cavitation nuclei have been eliminated from a channel along its length. Elimination may be achieved, for example, by application of hydrostatic pressure.

As the internal diameter of the tubing increases, however, the maximum oxygen concentration which can be perfused through its length into a 1 bar aqueous medium without cavitation inception is reduced. For example, the maximum oxygen concentration which can be used in this manner for a 100 micron internal diameter silica tubing is approximately 1.5 cc oxygen/g, while that for a 25 micron tubing is approximately 3 cc oxygen/g. Thus, larger bore capillary tubings can be used to deliver an effluent free of bubble formation, once cavitation nuclei are eliminated.

Accordingly, I have discovered an inverse relationship between the tubing internal diameter and the maximum oxygen concentration allowable. Channels as large as 1 mm or greater can probably be used, but the maximum oxygen concentration which can be achieved without bubble production in the effluent is less than that for the 100 micron tubing.

Experimental Procedure

Turning now to FIG. 1, a double-ended, high pressure vessel 10 (Leco, Tem-Press Div.) having a honed cylindrical cavity 12 with a 30 cc capacity was filled with a physiologic solution, for example, 5 g % dextrose in water from a container 14, equilibrated with oxygen at 700 psi. The oxygen-supersaturated fluid was transferred at 700 psi from a 300 cc capacity Parr bomb 16 after equilibration overnight. The Leco vessel was isolated from the Parr bomb. A piston, positioned at the proximal end of the Leco vessel and sealed with O-rings, was driven against the oxygen-supersaturated fluid at approximately 0.7 kbar hydrostatic pressure from a hydraulic compressor.

The fluid was delivered through a delivery system 18 including one or more exit ports, for example, a 100 micron internal diameter/363 micron outer diameter fused silica tubing (Polymicro Technologies) each of which having been tapered to 7 microns with a propane torch. After several minutes of hydrostatic compression to remove cavitation nuclei, it was determinated that no bubbles appeared in the effluent. This was confirmed by use of argon-ion laser illumination of fluorescein dye in the fluid. The silica tubing was then cleaved several millimeters proximal to the tapered section. The internal diameter at the distal end of the tubing then was 100 microns.

No cavitation inception occurred over a period of many hours, including refilling of the Leco vessel from the Parr bomb on multiple occasions. Even when the pressure in the Leco vessel was allowed to fall to 1 bar, no bubbles in the effluent, containing 1.1 to 1.5 cc oxygen/g, (expressed herein as M cc $O_2$/g) were noted. When a second 100 micron silica tubing containing cavitation nuclei was placed in parallel with the first tubing, a prominent stream of bubbles was ejected from the second tubing, and no bubbles were noted in the first tubing. However, after use of a tapered distal end and transient hydrostatic pressure to 0.7 kbar, no bubbles were noted in the second tubing after cleavage of the tapered tip so that the internal diameter at the distal end was 100 microns.

In a preferred system, a hydraulic compressor is used to apply 0.5 to 1.0 kbar liquid water pressure to eliminate cavitation nuclei on the inner surface of channels, such as those fabricated from multi-bore silica tubing, at the distal end of the delivery system. The liquid can either be either gas-depleted or gas enriched. Elimination of cavitation nuclei in the bulk gas-supersaturated liquid can be achieved simply by compression with gas at the desired partial pressure of the gas. Thus, when initiating flow through the silica tubing, high pressure liquid from the hydraulic compressor is used first, and subsequent flow of gas-supersaturated liquid is delivered from a reservoir Under pressure from a gas tank.

When $O_2$ gas compresses water before it is supersaturated, a combination of the gas pressure dissolving cavitation nuclei in the water and sufficient standing without excessive agitation eliminates bubbles.

Freestanding bubbles are inherently unstable—either they grow and rise to the surface or dissolve, although cavitation nuclei on the surfaces of the container or associated with motes may not disappear. Therefore, when gas-supersaturated water flows from the vessel pressurized from the $O_2$ tank, no bubbles in the effluent are noted. If an occasional bubble or a cavitation nucleus associated with a crevice in a mote flows through the tubing at the distal end of the delivery system, the stability of the effluent is unaffected. Very likely, when a bubble in the bulk liquid passes through the tubing, a thin film of liquid separates the bubble from the surface of the tubing, thereby inhibiting the formation of a cavitation nucleus. By contrast, if cavitation nuclei are present on the inner surface of the tubing, they generate rapid growth of bubbles continuously in the effluent.

The advantages inherent in the use of an $O_2$ gas source as the driving pressure for delivery of the $O_2$-supersaturated fluid include the fact that only one hydraulic compressor is needed to "prepare" the catheter for use. The hydraulic compressor very likely is then no longer needed. The volume of flow can be adjusted by simply using the appropriate number of channels for a given i.d. and length. The gas source would simultaneously provide the partial pressure required to achieve a desired concentration of gas in the water and the driving pressure for delivery of the gas-supersaturated water through the channels at the distal end of the delivery system. The gas pressure used for this dual purpose would be on the order of 100 to 2000 psi.

Alternatively, a hydraulic compressor is used to drive gas-supersaturated liquid through channels at the distal end of the delivery system. In order to maintain a relatively constant pressure, either two reciprocating hydraulic compressors would be used or a sufficiently large reservoir would be interposed between the compressor and the channels, such that the pressure drop in the reservoir occurring during refilling of a single compressor is not excessive.

A simple approach to achieve a high hydrostatic pressure, on the order of 0.5 to 1.0 kbar, within capillary channels to eliminate cavitation nuclei is to taper the distal end to a small diameter, on the order of <20 microns, prior to application of the pressure. Alternatively, relatively gas-depleted liquid can be perfused through larger channels at the same driving pressure. Although a pressure drop at the distal end of the channels reduces the degree of hydrostatic compression at this location, the relative lack of gas in the liquid helps to dissolve cavitation nuclei at the lower pressure. The gas-supersaturated water can then be delivered through the non-tapered distal end into water without cavitation inception. Once cavitation nuclei are eliminated, flow of oxygen-supersaturated water through the 100 micron tubing into water can be achieved without bubble formation in the effluent. The pressure in the high pressure vessel can then be lowered to 1 bar for many hours. With the distal end of the tubing stored in ordinary tap water overnight, flow of an oxygen-supersaturated water can be resumed without cavitation inception in the free stream.

Other ways may be used to eliminate cavitation nuclei throughout the length of the tubing. Temporarily blocking or capping the distal end of the channels to allow full hydrostatic pressure to be applied to the end of the channels prior to ejection (after removing the cap) is effective.

Alternatively, a scavenger of the gas may be deployed in the liquid within the tubing, prior to flow of the gas-supersaturated liquid. Examples of the latter approach for removing oxygen-containing gas nuclei along the surface of the channels include a sodium sulfite solution or a solution of deoxyhemoglobin. Either substance would bind oxygen and remove the gas nuclei.

Dissolution of cavitation nuclei on the inner surface of the channels requires a lower hydrostatic pressure when a more soluble gas compresses the nuclei. Therefore, perfusion of the channels with a solution of a highly soluble gas, such as carbon dioxide or a solution thereof can be used to exchange a relatively insoluble gas (e.g., air, or oxygen) in the nuclei for carbon dioxide. Dissolution of $CO_2$—containing cavitation nuclei can then be achieved at a relatively low level of hydrostatic compression because of the solubility of the gas. Although water dissolves carbon dioxide-containing nuclei, alternative liquids could be used, such as a perflurochemical, to dissolve cavitation nuclei containing soluble gase(s).

Electrochemical reduction of oxygen in gas nuclei within, for example, a metal tubing may be used at the distal end of the system for delivery of oxygen-supersaturated water to eliminate the nuclei.

Although application of a strong vacuum or heating the liquid within the tubing to a high temperature might be used to remove cavitation nuclei along the inner surface of the channels, hydrostatic compression of the liquid (particularly a degassed one if necessary) is preferable.

Removal of cavitation nuclei within the delivery system, particularly along the inner surface of channels at or near the exit port(s), where the hydrostatic pressure is relatively low, could be performed with a wide variety of additional alternative approaches. After placement of the distal end of the delivery system within a pressure fitting, liquid having a low gas content could be forced retrograde through the system, with or without flow. Temporarily freezing liquid near the exit port(s) would allow antegrade pressurization without flow, so that a relatively high pressure is maintained throughout. Likewise, temporary distal crimping of a high strength polymeric tube, such as polyamide or polyethylene terephthalate, if delivery channels were fabricated from a polymer, would allow antegrade pressurization to the distal end of the delivery system. Irrespective of the type of material used for the channels in the delivery system, perfusion of the channels with a liquid within which gases dissolve easily could be performed to facilitate removal of cavitation nuclei. Perfluorochemicals are an example of one such class of liquids.

As already noted, flushing the channels with a gas, such as carbon dioxide, having a high solubility in liquids prior to flushing the channels with a liquid would allow exchange of a gas, such as air or oxygen, having a relatively low solubility in liquids, with the highly soluble gas. Subsequent dissolution of cavitation nuclei containing the highly soluble gas could then be performed at a lower hydrostatic pressure.

Exposure of the distal end of the delivery system to ultrasonic energy or other methods of inducing vibration, whether mechanical or generated by an electromagnetic field during pressurization with a liquid would be expected to facilitate removal of gas nuclei. Chemical methods, beyond the aforementioned electrochemical and scavenger means, could be used to remove gas nuclei by exposure of the gas to one or more appropriate reagents. Many reagents are available which would react with oxygen, thereby removing gas nuclei containing this gas. Moreover, oxygen can be converted to a reactive oxygen species, such as a superoxide radical, by a variety of techniques. Such species can then react with many other molecules, thereby removing oxygen. Examples include the use of ionizing radiation, biologic enzymes, and photochemical reactions.

Finally, when either oxygen or carbon dioxide comprises the gas within the cavitation nuclei, viable organic matter suspended within the liquid in contact with the inner surface of the delivery system could be used to biologically consume the gas.

Undoubtedly, there are other means for removing cavitation nuclei, such as filtration methods, but the primary point to be made is that any suitable method for their removal will facilitate ejection of a gas-supersaturated effluent from a high pressure reservoir to a lower pressure environment without cavitation inception.

There are several advantages in the use of channels having an internal diameter larger than 10 microns: fewer number of channels are necessary to deliver an equivalent flow; adequate filtration of the gas-supersaturated liquid to prevent occlusion of the channels is simpler to achieve; and the flow rate and velocity can be adjusted more easily by use of channels or tubings having a suitable length.

For example, a 30 micron internal diameter fused silica tubing (Polymicro Technology), approximately 3 feet in length, will result in a flow velocity of approximately 200 cm/sec and a flow rate of approximately 0.09 cc/min, when oxygen-supersaturated 5 g % dextrose in water (approximately 3 cc oxygen/g) is pressurized to 0.7 kbar and delivered through the tubing into blood at physiologic pressure. Higher flow velocities may result in hemolysis, so that use of the appropriate length of the tubing is helpful in adjustment of the velocity to an appropriately low level. By use of a bundle of 30 micron internal diameter tubings, along with adjustment of the driving pressure between 1 bar to 1 kbar, after initial hydrostatic compression to 0.5 to 1 kbar, the overall flow rate can be varied to provide the desired rate of oxygen delivery.

While silica or glass capillary tubing is disclosed, channels may also be defined within quartz, a metal, hollow carbon fibers, a ceramic, sapphire, diamond, or a polymer. However, a hydrophilic material, such as glass, appears to be substantially more amenable to elimination of surface cavitation nuclei compared to hydrophobic materials. Application of a hydrophilic material to coat the surface of a delivery channel made of a hydrophobic material (for example, chemical vapor deposition methods, etc.) would be expected to improve the ability to remove cavitation nuclei at the surface.

It should be noted that there are a wide variety of geometries which could be employed at or near the exit port(s) which would permit the ejection of cavitation-free, gas-supersaturated liquid into a 1 bar environment from a high pressure reservoir. For example, I have found that a 50 micron diameter square borosilicate glass tubing works as effectively as both a round glass tubing and a round stainless steel tubing of similar diameter for this purpose. A rectangular or slit-like geometry characterizing the delivery channels would also be expected to be effective. If gas supersaturated liquid were delivered into the inner lumen of a coil, spring, or stacked rings, the pressure provided could be used to expand the space between the rungs or rings, thereby resulting in a circumferential slit. Alternatively, spacers placed at discrete locations about the circumference of stacked rings could be used to fix the size of the space between the rings during pressurization. In either case, the inner lumen would be occluded proximally and distally to allow flow of fluid exclusively between the rungs or rings.

As described in my copending application Ser. No. 152, 589, filed Nov. 15, 1993, delivery of an oxygen-supersaturated physiologic solution into a vein or a right heart chamber can be used for either partial or complete support of systemic oxygenation of patients. Intra-arterial delivery of the fluid can be used to achieve blood oxygen tensions much higher than that achievable by breathing oxygen to improve local oxygen delivery to hypoxic or ischemic tissues.

For example, I have been able to oxygenate blood in vitro in the following manner. Venous blood was exposed to nitrogen to lower the oxygen tension to very low levels, on the order of <20 mm Hg. Aliquots of 20 cc were placed in a plastic beaker and covered with Parafilm. One section of the wall of the beaker was replaced with a thin plastic film, so that an ultrasonic transducer could be positioned against the film, with an ultrasonic gel used as a coupling agent. A two dimensional image of the volume of blood was continuously monitored. An electrode (Diamond General, Ann Arbor) was placed within the blood for continuous monitoring of the partial pressure of oxygen.

One or more silica capillary tubings, having channel(s) ranging from 5 microns to 100 microns in internal diameter were used to deliver oxygen-supersaturated, cavitation nucleus-free 5 g % dextrose in water from a high pressure vessel (Leco) into the blood. The threshold partial pressure of oxygen at which multiple bubbles appeared by ultrasound was recorded. A mean partial pressure of oxygen of 800 to 900 mm Hg was achieved before the onset of bubble formation in approximately 20 runs.

Thus, the oxygen tensions achievable in blood are higher than 1 bar. Considering that, in a hyperbaric oxygen chamber, air is compressed rather than pure oxygen, the partial pressure of oxygen achievable in such chambers pressurized to 2-3 bar are on the order of only 350 to 650 mm Hg. In addition, high oxygen tensions in the compressed gas result in lung toxicity upon exposure for more than a few hours. Infusion of oxygen-supersaturated physiologic solutions into arterial blood, in contrast to the use of a hyperbaric chamber, can be used to achieve higher oxygen tension levels and do so for a much longer period of time. Treatment of local tissue hypoxia or ischemia by this approach can be achieved by placement of a catheter within the arterial blood supply of the target tissue.

Table A discloses examples of and derivations from experimental observations made during the practice of the present invention. When an $O_2$ gas source is used to provide the driving pressure, at 10 to 150 bar, the minimum length is reduced by a factor equal to the ratio of the gas pressure to 0.7 kbar.

TABLE A

EXAMPLES DERIVED FROM EXPERIMENTAL OBSERVATIONS

| Internal Diameter Of Silica Tubing Microns | Max. Flow/Tube cc/min | Min. Length cm | Max. Oxygen cc/g | No. of Tubes | Flow Rate g/min. | Diameter of Bundle mm |
|---|---|---|---|---|---|---|
| 100 | 0.94 | 1006 | 1.5 | 35 | 33.0 | 0.84 |
| 50 | 0.24 | 252 | 2.2 | 95 | 23.0 | 0.69 |
| 25 | 0.059 | 63 | 3.0 | 282 | 17.0 | 0.59 |
| 15 | 0.021 | 22.6 | 3.3 | 722 | 15.0 | 0.57 |
| 10 | 0.0094 | 10.1 | 3.6 | 1478 | 14.0 | 0.54 |
| 6 | 0.0034 | 3.6 | 4.0 | 3676 | 12.5 | 0.51 |
| 5 | 0.0024 | 2.5 | 4.1 | 5081 | 12.2 | 0.50 |
| 4 | 0.0015 | 1.6 | 4.2 | 7937 | 11.9 | 0.50 |
| 3 | 0.00085 | 0.91 | 4.4 | 13369 | 11.4 | 0.49 |
| 2 | 0.00038 | 0.4 | 4.8 | 27412 | 10.4 | 0.47 |
| 1 | 0.000094 | 0.1 | 5.0 | 106383 | 10.0 | 0.46 |
| 0.5 | 0.000024 | 0.025 | 5.2 | 400641 | 9.6 | |
| 0.25 | 0.0000059 | 0.0063 | 5.4 | 1569366 | 9.3 | |

NOTE: The number of tubes describes the capillary array at the distal end of the catheter. The maximum oxygen delivery at 0.7 kbar equaled 50 cc's of oxygen per minute for each diameter. The minimum length is based on a maximum flow velocity of 200 centimeters per second. Though higher velocities are possible, prolonged use of higher velocities may result in hemolysis of red cells.

Other Uses

A. MRI

Since oxygen is paramagnetic, infusion of oxygen-supersaturated solutions into blood would be expected to enhance imaging of blood and oxygenated tissues by magnetic resonance imaging (MRI). That is, an oxygen-supersaturated solution would be expected to act as an MRI contrast agent.

B. Non-Intravascular Medical Applications

If oxygen-supersaturated physiologic solution or water were placed in contact with a body surface, including skin and wounds, a marked increase in the rate of diffusion of oxygen into tissue would occur, since the partial pressure of the gas could be made to be as high as approximately 140 bar.

In addition, as water diffuses across a body surface, oxygen in the gas-supersaturated fluid would be transported, thereby enhancing the rate of diffusion of the gas into tissue.

In wounds which are ischemic, the improved oxygen levels in tissue would increase the rate of healing. For a large surface area to mass ratio, such as in young infants or neonates, contact of most of the surface area of the body (excluding the head) with oxygen-supersaturated fluid may result in a significant increase in blood oxygen tension levels, when oxygenation by ventilation alone is associated with systemic hypoxemia.

Ventilation with oxygen-supersaturated physiologic solutions may be used to support systemic oxygenation in patients with respiratory insufficiency. Inflation of atelectatic regions of the lung with oxygen-supersaturated liquids would be more effective than air or $O_2$ gas in expanding alveoli and more effective in enhancing oxygen diffusion to pulmonary capillaries. In addition, inflation of the lung with the liquid would simultaneously be useful to remove unwanted lung exudates.

Infusion of oxygen-supersaturated fluids (for example, physiologic crystalloid solutions, perfluorochemicals, mixtures thereof) into either the cerebrospinal fluid space or the peritoneal cavity would be expected to enhance oxygen delivery to the central nervous system (for treatment of conditions such as stroke) and to systemic or gastrointestinal tissues, respectively. It should be apparent that oxygen-supersaturated fluids could also be injected directly into a target tissue such as a tumor to enhance the response to radiation therapy.

Topical application of oxygen-supersaturated solutions to wounds, in addition to relieving tissue hypoxia, could be used to clean, debride, and sterilize such tissues. Hydrogen peroxide solutions are used currently for these purposes, but cells-within granulation tissue may be damaged along with bacteria by peroxide solutions. In contrast, a hyperbaric oxygen solution would be toxic to bacteria and beneficial to tissue within the wound.

Immersion of a bodily part, such as an arthritic joint or foot with a poorly healing ischemic ulcer, into a container with oxygen-supersaturated fluid would be expected to increase oxygen delivery to these tissues and promote healing.

To my knowledge, there are no published references discussing the potential use of oxygen-supersaturated solutions for enhancing oxygen transport into biologic tissues. It should be apparent, therefore, that the concept of bringing oxygen-supersaturated fluids in contact with biologic tissues by any method, for increasing oxygen transport to tissues, is novel. Although a continuous infusion of oxygen-supersaturated fluid from a high pressure vessel to a 1 bar environment is the preferred method, other means could be employed to allow contact of the fluid with tissue. For example, after preparing an oxygen-supersaturated fluid in a high pressure vessel in a manner which produces a relatively bubble-free and cavitation nuclei-free solution, the pressure can be released to approximately 1 bar. The vessel could then be opened quickly (for example, a quick release clover leaf opening in a large pressure vessel rated at a maximum operating pressure of 30,000 psi is available from High Pressure Equipment Corp.). The oxygen-supersaturated fluid could then be poured from the vessel onto tissue or into another container within which the tissue is immersed. In addition, after decanting the fluid, it could be transferred into a syringe for subsequent ejection into tissue. Although water is the preferred liquid medium, other liquids, such as perfluorochemicals, could also be used in this manner.

Contact of an oxygen-supersaturated solution with a semipermeable membrane would facilitate transport of the gas across the membrane. Therefore, use of an oxygen-supersaturated solution in a membrane oxygenator to deliver oxygen into blood may be a more efficient method of blood oxygenation compared to the use of oxygen gas at or near 1 bar.

C. Industrial Applications

The ability to inject a gas-supersaturated fluid into a relatively low pressure environment without immediate cavitation inception finds utility in many industrial applications. The following applications are representative examples.

1. Fire Extinguishing. When cavitation-free, gas-supersaturated water is ejected at a high velocity from the distal end of a tube, gas nucleation occurs after breakup of the stream into droplets because of the inherent tensile strength of water. If an inert gas, such as nitrogen, carbon dioxide, or argon is dissolved in water at a supersaturated concentration and compressed to remove cavitation nuclei, a stream of water containing the gas under high pressure can be delivered into a 1 bar air or liquid environment without cavitation taking place near the exit port.

For example, nitrogen can be dissolved at a pressure of approximately 150 bar in water either before or after 0.5 to 1.0 kbar hydrostatic compression of water along channels in the delivery system to remove cavitation nuclei. The stream of water that can be ejected from a suitable tubing preserves the metastability of the fluid by the absence of cavitation nuclei. Upon contact of the gas-supersaturated stream of water with solid surfaces, spontaneous breakup into droplets occurs and the gas is released suddenly. A similar result follows heating.

To extinguish a fire, the gas release will be beneficial in at least 3 ways. The expansion of the gas will aid the dispersion of water over a broader volume; expansion of gas results in cooling; and the inert gas will displace oxygen in the air. Although this method of extinguishing a fire would be expected to be more costly, it should make more efficient use of water and, more importantly, it should be more effective than the conventional use of water. Such benefits are enhanced in draught-stricken areas and in other situations where there is difficulty in delivering enough extinguishing water to the incendiary area.

I conducted a test of this application in the following manner. A jet stream of water, delivered from a high pressure vessel at 0.7 kbar and having a velocity of approximately 2,000 cm/sec through a 10 micron i.d. silica tubing, was directed at the flame of a laboratory propane torch. The flow rate of propane was adjusted so that the apex of the inner blue portion of the flame coincided with the end of the metal collar. Starting with a distance of about 8 inches between the distal end of the silica tubing and the apex of the blue portion of the flame, the distance was reduced until the flame was either extinguished or the distance was less than 1 inch.

With no gas in the water, a mean distance of 2 to 3 inches was required in 3 runs to extinguish the flame. In one run, the flame could not be extinguished. In another, a distance of approximately 1 inch was required.

In contrast, when water was supersaturated with argon at 1700 psi (approximately 3 cc gas/g) and hydrostatically compressed to 0.8 kbar to eliminate cavitation nuclei, a mean distance of approximately 4.5 to 5 inches was effective in abolishing the flame in each of 4 runs. The silica tip and flow conditions for these runs were identical to those without gas in the water.

Thus, it is clear that the use of water supersaturated with an inert gas, stabilized by hydrostatic compression and use of the tapered silica tip, was far more effective than the use of water alone for extinguishing the flame of the propane torch.

If a highly water soluble, inert gas such as carbon dioxide, is used, the hydrostatic pressure used to dissolve gas nuclei and gas pressures used to provide a useful concentration would be much lower.

2. Purification and Carbonation of Beverages. Water used for human consumption undergoes multiple steps to ensure purity and lack of contaminants which could affect either health or taste. One commonly used initial step is chemical treatment to oxidize contaminants.

Infusion of oxygen-supersaturated, cavitation-free water is a more efficient method of oxidation than the use of oxygen gas (since oxygenation of water by convection is more efficient that by diffusion), and would be nontoxic, in contrast to the use of peroxides.

Once water for the beverage has been purified, carbon dioxide is usually introduced prior to sealing it in a bottle or can (or an undercover gasser may be used for cans). The gas is usually introduced under high pressure at a low temperature in order to increase its dissolved concentration. The use of water supersaturated with carbon dioxide and treated to remove all cavitation nuclei would allow the process of carbonation to be conducted at virtually any ambient room temperature, thereby obviating the need for cooling. If the inside walls of the containers were also free of significant cavitation nuclei, it should be possible to store the beverage at room temperature and to open the container at the higher than usual temperature without prominent bubble evolution and without rapid loss of the carbonation.

An interesting alternative to the use of carbon dioxide to provide effervescence in beverages is the use of oxygen, air, or nitrogen. The limited solubility of these gases ordinarily precludes their use for this purpose. However, by mixing water supersaturated with any of the gases with a syrup concentrate immediately before consumption, a gas yield of the resultant beverage would be similar to that currently used in carbonated beverages. In a simple test, I mixed non-carbonated cola (pharmaceutical grade) syrup with an equal volume of oxygen-supersaturated 5 g % dextrose in water (2 cc oxygen per gram). The resultant beverage had an effervescence and taste equivalent to those of carbonated colas.

When oxygen or air is used in this manner, the hyperbaric oxygen content in the beverage would help maintain sterility, and its consumption would be expected to have a more favorable inhibitory effect on bacterial pathogens in the oral cavity compared to the use of carbon dioxide.

3. Steelmaking. During the process of making steel, an oxygen "lance" is used to deliver oxygen gas initially to the surface of the crude metal melt and subsequently to deeper layers with the help of cooling water jets adjacent to the high velocity oxygen. The purpose of the oxygen treatment is to oxidize undesirable materials such as carbon and silicon. The frothy mixture which is produced floats at the top of the melt and is poured off, leaving the purified molten steel.

The use of water supersaturated with oxygen would be expected to be more effective in penetrating the molten metal compared to the stream of oxygen gas. The oxidation process would therefore be more rapid and complete, resulting in a steel having superior yield characteristics and a more efficient method.

4. Delignification of Wood Pulp. Bleaching of wood pulp and its delignification require oxygen which is introduced either as a gas or in the form of hydrogen peroxide. The use of oxygen supersaturated water would be a far more efficient means of oxygenation of the slurry containing the wood pulp, and higher levels of oxygen tension could be obtained compared to the use of oxygen gas.

Following such treatment, the effluent would be less toxic compared to the use of hydrogen peroxide. In addition, the latter would be expected to be more expensive than the use of oxygen-supersaturated water.

Bleaching of any type of material, in general whether in industry or in private homes, with oxygen-supersaturated water would be expected to produce an effluent which is less toxic to the environment than that associated with the use of a peroxide.

5. Wastewater/Bioreactor Treatment. All currently available methods of treatment of wastewater are based on some means of mixing air or oxygen gas with water and rely on the slow process of diffusion from the gas to the liquid phase for oxygenation of the wastewater. Similarly, most methods for introducing oxygen into bioreactors, which are used to produce a byproduct such as a drug, rely on mixing oxygen gas with water within which organisms are suspended. The rate of oxygen consumption by some organisms is quite rapid, so that introducing oxygen sufficiently rapidly has inspired the design of many types of bioreactors.

The basic mass transfer steps (i.e. the steps through which oxygen must pass) in moving from air (or oxygen-enriched air) to the reaction site in a biological species consist of: transport through the gas film inside the bubble; across the bubble-liquid interface; through the liquid film around the bubble; across the well-mixed bulk liquid (broth); through the liquid film around the biological species; and finally transport within the species (e.g. cell, seed, microbial species) to the bio-reaction site. Each step offers a resistance to oxygen transfer. The rate-limiting step typically occurs at the air-liquid interface.

The use of oxygen supersaturated water would be far more rapid than currently available methods, since (as noted earlier) oxygenation by convection is significantly more rapid than by diffusion, and would allow fine control of the optimal partial pressure of oxygen within the bioreactor.

In the biotechnology field, the supply of oxygen to a growing biological species (aeration) in an aerobic bioreactor is one of the most critical requirements in biotechnology. Aeration is usually accomplished by transferring oxygen from the air into the fluid surrounding the biological species from whence it is, in turn, transferred to the biological species itself. The rate at which oxygen is demanded by the biological species in a bio-reactor depends on the species, its concentration, and on the concentration of other nutrients in the surrounding fluid.

The main reason for the importance of aeration lies in the limited solubility of oxygen and water, a value which decreases in the presence of electrolytes and other solutes as temperature increases. A typical value for the solubility of oxygen (the equilibrium saturation concentration) in water at atmospheric pressure at 25° C. is about 0.03 cc oxygen per gram.

In addition to each bio-reaction demanding oxygen at a different rate, there is a unique relationship for each between the rate of reaction and the level of dissolved oxygen. Introduction of oxygen-supersaturated water into a bioreactor or wastewater would allow both rapid and precise control of the optimal oxygen concentration.

6. Oxygenation of Pond, Lakes, Streams, Aquariums, Fisheries, Swimming Pool, and Municipal Drinking Water. In order to promote an aerobic environment in these bodies of water, oxygen within air is mixed within the water. As noted above, this process is inefficient because of the relatively slow process of diffusion from the gas phase into the liquid.

Injection of air- or oxygen-supersaturated water into such bodies of water would not only be a far more efficient means of transfer of oxygen, but a high velocity stream of the gas-supersaturated water would penetrate far more effectively into large bodies of water than either a gas or a gas/water mixture. The stream could be directed from a more superficial location to penetrate deep layers of water, in contrast to the need to position a gas/water mixing apparatus or a bubble generator within deep layers of water.

7. Cleaning of Surfaces. Water jets are commonly employed to clean surfaces of factory floors, the exterior of buildings, bridges, gas (e.g., air).

Supersaturated water would be expected to be more efficient, since the sudden expansion of the gas upon contact with the surface would provide an additional force for removal of surface materials. Cavitation inception upon contact with the surface would act in a similar manner to the action of sandblasting, but would not, in contrast, pose an environmental concern.

8. Enhancement of Chemical Reactions. When a chemical reaction involves the use of a gas in a liquid medium, the rate of reaction at ambient pressure will be enhanced by the use of a gas-supersaturated liquid. In addition, in exothermic reactions, wherein it is desirable to avoid an excessive rise in temperature, the liquid carrying the gas at a supersaturated concentration could be used as ballast.

Injection of water supersaturated with either oxygen or air into or onto an organic fuel for enhancement of combustion and control of temperature represents one such example. Similarly, if liquid fuel is supersaturated with air or oxygen and cavitation nuclei have been removed within the delivery system containing the gas-supersaturated fuel, combustion of the fuel upon its ejection from the high pressure vessel and upon ignition would be expected to proceed more rapidly than the use of the fuel alone. The high pressure of oxygen within the fuel, along with a broad surface area presented when the stream of fuel breaks up into droplets and subsequently microscopic bubbles, would be responsible for the improved rate of combustion.

9. Snowmaking. With the use of conventional snowmaking equipment, e.g., for recreational skiing, the ice particles are produced before ejection into the atmosphere. Therefore, the distance which the snow can be blown with air is limited.

When air-supersaturated water is ejected at a high velocity into ambient air, cavitation nuclei are formed after breakup of the stream into a fine mist. During expansion of gas, nuclei form during or after breakup of the stream into a mist, and the temperature of each droplet will fall as a result of expansion of the gas.

Strobe light photography at a 20 ns exposure (Xenon Corp.) under a light microscope has demonstrated that each droplet of gas-supersaturated water is transformed into a bubble. If the temperature of the water is near 0° C. at the time of ejection from a high pressure reservoir, the fall in temperature will convert each droplet into a particle of ice or snow.

Use of water at high pressure has the additional advantage of depressing its freezing point. For example, at 1 kbar, the freezing point of water is approximately −11° C. Thus, the water could be ejected at a temperature even below 0° C., and gas expansion would cool the resultant ice particles to a yet lower temperature. Ejection of a stream of water, supersaturated with air, into the atmosphere could be used to cover much greater distances than that achievable with conventional snowmaking equipment. Fewer machines would be required with this method to cover the same area with artificial snow, which would be a more efficient and, very likely, more economical means of snowmaking.

10. Other Uses. The physical and chemical properties of a liquid supersaturated with a gas differ from either that of the liquid or the gas. Such properties are too numerous to elaborate, but include, in alphabetical order, the boiling point, chemical potential, compressibility, density, dielectric constant, enthalpy, free energy, heat capacity, magnetic susceptibility, specific heat, surface tension, thermal conductivity, and viscosity.

The ability to use a liquid supersaturated with a gas at a relatively low pressure is the basis of most applications of the present invention. Accordingly, use of any physical or chemical property of gas-supersaturated liquids, stabilized during ejection from a high pressure reservoir to a low pressure environment, thereby avoiding cavitation inception at or near the exit port, falls within the scope of the invention.

I claim:

1. A method of injecting gas-supersaturated fluids as a bubble-free effluent from a delivery system into a gas-depleted industrial environment, comprising the steps of:

a. eliminating cavitation nuclei from within the delivery system;

b. compressing a liquid and a gas to form a gas-supersaturated liquid;

c. positioning the delivery system in fluid communication with the industrial environment; and d. ejecting the gas-supersaturated liquid through the delivery system from an exit port as an effluent into the industrial environment without associated cavitation formation in the effluent at or near the exit port.

2. The method of claim 1 wherein the cavitation nuclei in the delivery system are removed by hydrostatic compression with a liquid having a relatively low concentration of the nuclei.

3. The method of claim 1 wherein the cavitation nuclei in the delivery system are removed by hydrostatic compression with the gas-supersaturated effluent.

4. The method of claim 1 wherein the cavitation nuclei in the delivery system are removed by perfusion with a solution containing a scavenger of the nuclei.

5. The method of claim 1 wherein the cavitation nuclei in the delivery system are removed electrochemically.

6. The method of claim 1 wherein the cavitation nuclei in a delivery system are removed by blocking the distal end of the delivery system and applying hydrostatic pressure.

7. The method of claim 1 wherein the cavitation nuclei in the delivery system are removed by applying a vacuum during immersion of the delivery system in a liquid.

8. The method of claim 1 wherein the gas is dissolved in the liquid at a high partial pressure of the gas prior to compression of the liquid.

9. The method of claim 1 wherein the liquid is hydrostatically compressed prior to exposure to a high partial pressure of the gas.

10. The method of claim 1 wherein aliquot parts of the gas and the liquid are hydrostatically compressed together.

11. The method of claim 1 wherein the hydrostatic pressure is varied over a 1 bar to 1.0 kbar range after transient application of a 0.1 to 1.0 kbar pressure to dissolve cavitation nuclei of a relatively insoluble gas along the inner surface of the delivery system.

12. The method of claim 1 wherein the hydrostatic pressure is varied over a 1 bar to 1.0 kbar range after transient application of a 5 bar to 1.0 kbar pressure to dissolve cavitation nuclei of a relatively soluble gas along the inner surface of the delivery system.

13. The method of claim 1 wherein the delivery system includes channels each having an internal diameter in a range of 0.1 micron to approximately 1 cm.

14. The method of claim 1 wherein the liquid is water.

15. The method of claim 1 wherein the gas is oxygen.

16. The method of claim 1 wherein the gas is an inert gas.

17. The method of claim 1 wherein the gas is air.

18. The method of claim 1 wherein the gas is carbon dioxide.

19. A method of injecting gas-supersaturated fluids as a bubble-free effluent from a delivery system into a gas-depleted industrial environment, comprising the steps of:

a. eliminating cavitation nuclei from within the delivery system including an exit port having an internal diameter D:

b. compressing a liquid and a gas to form a gas-supersaturated liquid having a maximum concentration of the gas in the liquid expressed as M units of volume of the gas per unit weight of the liquid;

c. positioning the delivery system in fluid communication with the industrial environment; and d. ejecting the gas-supersaturated liquid through the delivery system from an exit port as an effluent into the industrial environment without associated cavitation formation in the effluent at or near the exit port, such that there is an inverse relationship between D and M.

20. The method of claim 19, wherein the delivery system comprises a bundle of tubings.

21. The method of claim 1, wherein the gas-supersaturated liquid comprises a liquid fuel supersaturated with a gas selected from the group consisting of air, oxygen, and mixtures thereof so that combustion of the fuel upon its ejection from the delivery system may proceed more rapidly than would be the case if the fuel alone were ignited.

22. The method of claim 21, wherein the step of eliminating cavitation nuclei from within the delivery system comprises the step of perfusion by the gas-supersaturated fuel, an improved rate of combustion being produced by the high pressure of oxygen within the fuel in combination with a broad surface area presented when a stream of the fuel breaks up into droplets and subsequently into microscopic bubbles.

23. The method of claims 14 or 15 or 17 wherein the environment is a bioreactor.

24. The method of claims 14 or 15 or 17 wherein the environment is wastewater.

25. The method of claims 14 or 15 or 17 wherein the environment is potable water.

26. The method of claims 14 or 15 or 17 wherein the environment is a fishery.

27. The method of claims 14 or 15 or 17 wherein the environment is a lake, pond, stream, swimming pool, or municipal water.

28. The method of claims 14 or 15 or 17 wherein the environment is a slurry of wood pulp.

29. The method of claims 14 or 15 or 17 wherein the environment is molten metal.

30. The method of claims 14 or 16 wherein the environment includes materials undergoing combustion.

31. The method of claim 1 wherein the environment is within a chemical reactor.

32. The method of claims 14 or 17 wherein ejection of air-supersaturated water into ambient air at a temperature near 0° C. produces ice or snow.

33. The method of claim 1 wherein the environment is a semi-permeable material.

34. The method of claims 14 or 15 wherein the environment is a beverage.

35. The method of claim 1 wherein the environment is a surface to be cleaned.

36. The method of claim 1, wherein the gas-supersaturated liquid comprises water supersaturated with a gas selected from the group consisting of oxygen, air, and mixtures thereof, the environment comprising an organic fuel so that combustion is enhanced and temperature is controlled.

37. The method of claim 1, wherein the gas is nitrogen.

38. The method of claim 1, wherein the gas is argon.

* * * * *